United States Patent [19]

Whitesides et al.

[11] 4,440,854

[45] Apr. 3, 1984

[54] PREPARATION OF 6-DEOXY-D-FRUCTOSE AND 6-DEOXY-L-SORBOSE

[76] Inventors: George M. Whitesides, 124 Grasmere St., Newton, Mass. 02160; Francois P. Mazenod, 16 Cite Vieusseux, 1203 Geneve, Switzerland; Chi-Huey Wong, 402 Rindge Ave., Apt. 15F, Cambridge, Mass. 02139

[21] Appl. No.: 422,070

[22] PCT Filed: Apr. 23, 1982

[86] PCT No.: PCT/US82/00534

§ 371 Date: Aug. 30, 1982

§ 102(e) Date: Aug. 30, 1982

[51] Int. Cl.³ .................... C12P 19/24; C12P 19/02; C07H 3/08
[52] U.S. Cl. ..................................... 435/94; 435/105; 536/1.1; 536/124; 536/125
[58] Field of Search .................. 435/94, 105; 536/1.1, 536/124, 125

[56] References Cited

PUBLICATIONS

Matsui et al., Chemical Abstracts 91:20309q, 1979.
Kaufmann et al., Chemical Abstracts 68:39963v, 1968.

*Primary Examiner*—Lionel M. Shapiro
*Attorney, Agent, or Firm*—Arthur A. Smith, Jr.; Thomas J. Engellenner

[57] ABSTRACT

6-Deoxy-D-fructose and 6-deoxy-L-sorbose, useful starting materials for the synthesis of 4-hydroxy-2,5-dimethyl-2,3-dihydrofuran-3-one, are obtained from fructose-1,6-diphosphate by a reaction with lactaldehyde, in the presence of an enzymatic system composed of aldolase and triose phosphate isomerase (TPI) in an aqueous medium at pH 7.0, followed by the hydrolysis of the monophosphate salt thus obtained. The same deoxy-sugars are obtained by the reaction between 1,3-dihydroxyacetone phosphate and lactaldehyde in the presence of the same enzymatic system composed of aldolase and TPI. The aforementioned deoxysugars are also prepared by the reaction of 1,3-dihydroxyacetone with lactaldehyde in the presence of an anionic exchange resin.

3 Claims, No Drawings

PREPARATION OF 6-DEOXY-D-FRUCTOSE AND 6-DEOXY-L-SORBOSE

The Government has rights in this invention pursuant to Grant Number NIH-5-R01-GM26543-03 awarded by the U.S. Department of Health and Human Services.

TECHNICAL FIELD

This invention relates to organic chemical synthesis and, in particular, synthesis of 6-deoxy sugars.

BACKGROUND OF THE INVENTION

The 6-deoxy sugars constitute particularly useful starting materials for the preparation of 4-hydroxy-2,5-dimethyl-2,3-dihydrofuran-3-one, better known by the name of FURANEOL ® (registered trademark of Firmenich SA, Geneva). M. Matsui et al. [see Chem. Abstr., 91, 20309q (1979)], for example, have described the method for converting 6-deoxy-D-glucose into FURANEOL. Although the yields observed during this conversion were very satisfactory, the method of Matsui suffers from a major drawback, i.e., the high cost of the starting material whose preparation requires four reaction steps. This invention concerns an original solution to this problem. We have found that 6-deoxy-D-fructose and 6-deoxy-L-sorbose, of the following formulas respectively

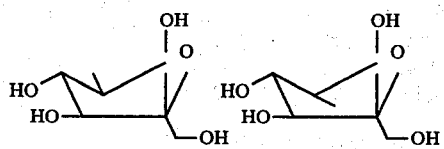

can be converted into FURANEOL in excellent yield, with the conversion taking place in the presence of an organic nitrogen base and a carboxylic acid, under reaction conditions similar to those described by Matsui.

SUMMARY OF THE INVENTION

This invention concerns a process for the preparation of 6-deoxy-D-fructose and/or 6-deoxy-L-sorbose characterized by the fact that the following steps are carried our consecutively:

a. Treatment of fructose-1.6-diphosphate with D- and/or L-lactaldehyde in the presence of an enzymatic system composed of aldolase and triose phosphate isomerase in aqueous medium at pH 7.0, and b. Hydrolysis of the monophosphate salt thus obtained. This invention also concerns a process for the preparation of 6-deoxy-D-fructose and/or 6-deoxy-L-sorbose which consists of treating 1.3-dihydroxyacetone phosphate of the formula

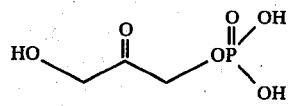

with D- and/or L-lactaldehyde in the presence of an enzymatic system composed of aldolase and triose phosphate isomerase in equation medium at pH 7.0, and hydrolyzing the monophosphate salt thus obtained.

This invention finally concerns a process for the preparation of 6-deoxy-D-fructose and/or 6-deoxy-L-sorbose which consists of treating 1.3-dihydroxyacetone with D- and/or L-lactaldehyde in the presence of an anionic exchange resin.

The processes described above can be illustrated by the reaction scheme below:

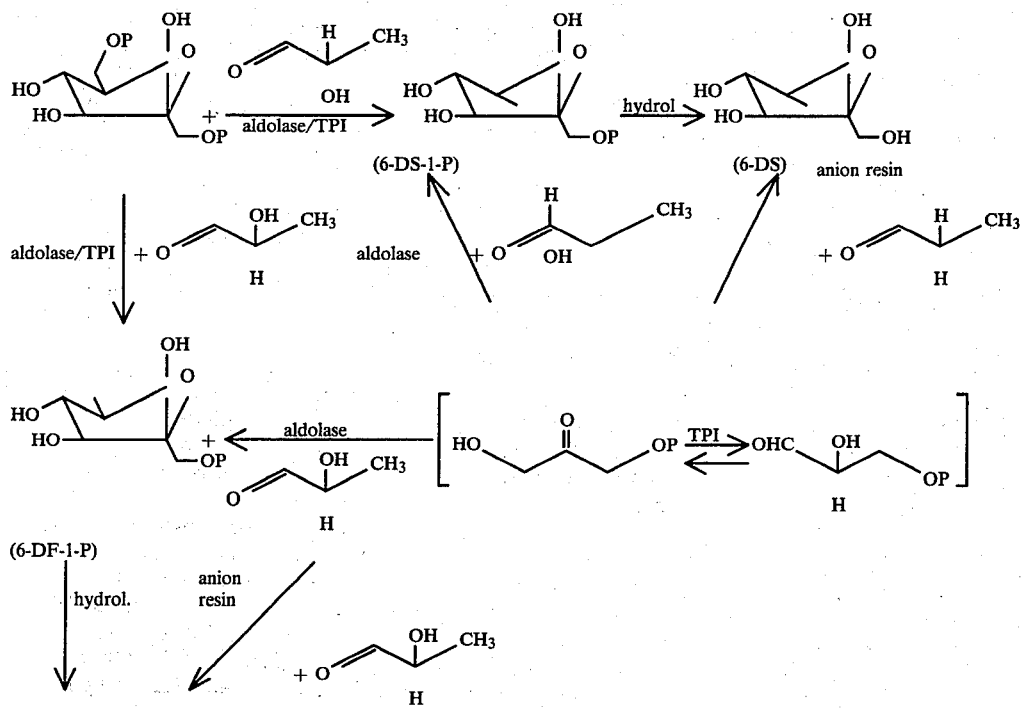

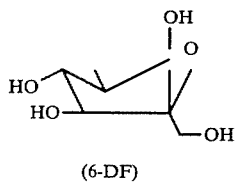

(6-DF)

Definition of abbreviations:
6-DF=6-deoxyfructos; 6-DF-1-P=6-deoxyfructose-1-phosphate
6-DS=6-deoxysorbose; 6-DS-1-P=6-deoxysorbose-1-phosphate
TPI=triose phosphate isomerase.

The first step of the procedures making use of aldolase and triose phosphate isomerase (TPI) formally constitutes an example of aldol condensation. This reaction proceeds in a perfectly selective manner and does not require the protection of other functional groups present in the molecule. The required reaction conditions are also particularly mild (pH 7.0-room temperature), and it follows that the industrial application of the aforementioned procedures for the preparation of 6-deoxy-D-fructose or 6-deoxy-L-sorbose can be visualized directly. The enzymatic system chosen was immobilized on a solid support in accordance with the method described in J. Am. Chem. Soc., 102, 6324 (1980). The aldolase and the triose phosphate isomerase are commercial enzymes.

The D- and L-lactaldehyde were prepared from L- and D-threonine by reaction with ninhydrin according to the method described in J. Biol. Chem., 241, 3028-35 (1966).

The 1,3-dihydroxyacetone phosphate (DHAP) can be obtained either by enzymatic phosphorylation of 1,3-dihydroxyacetone (DHA) using ATP and the monopotassium salt of phosphoenolpyruvate, or by the chemical phosphorylation of the same DHA using $POCl_3$. Fructose-1,6-diphosphate, in the form of its sodium or dicalcium salt, is a commercial product. If necessary, it can be purified before its use by a treatment using an anionic exchange resin, for example, of the type DOWEX 1. The particular purification method used is described in detail in the examples which follow.

As indicated above, one of the procedures which consists of the reaction between 1,3-dihydroxyacetone and lactaldehyde is carried out in the presence of an anionic exchange resin.

For this purpose, AMBERLITE ® (see The Merck Index, 9th Edition, Merck & Co. Inc., USA, Sec. 386) Type IRA-400 is preferably used.

The deoxyfuranoses prepared in accordance with the procedures described above can be used directly for their conversion into FURANEOL.

DESCRIPTION OF THE PREFERRED EMBODIMENTS

The invention is illustrated in a more detailed manner by the following examples, in which the temperatures are indicated in degrees Centigrade and the abbreviations have the meanings customary in the art.

EXAMPLE 1 a. 6-Deoxy-D-fructose-1-phosphate (6-DF-1-P) 100 ml of an aqueous solution containing fructose-1,6-diphosphate (20 mmoles; solution prepared from its barium salt by treatment with a type DOWEX 50 anionic exchange resin and neutralization with a solution of NaOH) and 25 mmoles of D-lactaldehyde (pH=7.0) was deoxygenated with argon.

An enzymatic system composed FDP-aldolase (500 U, 15 ml of gel) and triose phosphate isomerase (200 U, 1 ml of gel) coimmobilized on a solid support of polyacrylamide was added to the aqueous solution of FDP at room temperature and with vigorous agitation. The progress of the reaction was followed by enzymatic analysis. The reaction took 2½ days. After separation of the gel, the solution was mixed with 45 mmoles of $BaCl_2$ and the pH was adjusted to 7.8 at 4°. At this temperature, 1 liter of acetone was added, which induced the formation of a precipitate (14.8 g) containing 34 mmoles (yield 87%) of the barium salt of 6-deoxy-D-fructose-1-phosphate (6-DF-1-$PBa_2$). The enzymatic activities of the recovered aldolase and isomerase were 78% and 75%, respectively.

NMR(250 MHz, $D_2O$): 1.33 and 1.35 (3H, d); 3.6–4.2 (5H, m) δ ppm.

b. 6-Deoxy-L-sorbose-1-phosphate (6-DS-1-P) This compound was prepared in accordance with the procedure described under letter a., using L-lactaldehyde. The yield obtained was 80% of a product with a purity of 86%.

NMR(250 MHz, $D_2O$): 1.18 and 1.29 (3H, d); 3.4–4.5 (5H, m) δ ppm.

c. (6-DF-1-P) and (6-DS-1P) The mixtures containing (6-DF-1-P) and (6-DS-1-P) at the same time were prepared by the procedure described under letter a. above, starting with 0.2 moles of fructose-1.6-diphosphate and 0.3 moles of DL-lactaldehyde and in the presence of 25 ml of aldolase gel (100 U) and 3 ml of triose phosphate isomerase gel (500 U). The product was isolated in the form of the barium salt (152 g; 328 mmoles) with a purity of 82% (yield 82%).

The 6-deoxyfructose and the 6-deoxysorbose are prepared from the respective phosphates as follows:

10 mmoles of the phosphate salt obtained as indicated above was suspended in 50 ml of water and the mixture was treated with 10 g of a DOWEX 50 acid exchange resin. The acidic solution obtained (pH 1.0), after filtration, was heated at 90° for 8 h, and then a basic DOWEX 1 exchange resin was added until the solution reached a pH of approximately 6-7 at 25°. The mixture was then filtered and the clear filtrate was concentrated to eliminate the water present. A mixture of methanol (10 ml) and acetone (10 ml) was added to the residue and the precipitate which resulted from this was separated. The clear solution was then concentrated until an oily residue was obtained, composed of the desired deoxy-sugar.

6-Deoxy-D-fructose($D_2O$,DSS,250 MHz): 1.32 (3H,d,J=6.1); 3.52 (1H,q);

3.65–3.88 (2H,m); 4.06 (1H,m); 4.88 (1H) δ ppm; 6-Deoxy-L-sorbose ($D_2O$,DSS,250 MHz): 1.16 (3H,d,J=6.7); 1.27 (3H,d,J=6.1);

3.55 (2H,d,J=4.9); 4.05 (1H,d,J=4.3); 4.18 (1H,m); 4.38 (1H,m); 4.84 (1H) δ ppm.

The barium salt of fructose-1,6-diphosphate, used as the starting material in the procedure described above, was prepared as follows:

20 g of the dicalcium salt of fructose-1,6-diphosphate (commercial product with a purity of 63%) in 300 ml of water was treated with 400 g of type DOWEX 50 acid exchange resin. After filtration and washing with 100 ml of water, the solution was passed through a sintered glass filter containing 400 g of a basic DOWEX 1 exchange resin. It was then washed with dilute HCl (2.5 liters). 90 mmoles of barium chloride was added to the solution obtained, the pH of which was brought to 8.0 by the addition of a solution of NaOH. 500 ml of ethanol was then added to the solution cooled to 4°, and 28 g of the precipitate thus formed was collected by filtration. An enzymatic analysis using aldolase and glycerol phosphate dehydrogenase indicates a content of 86% of the barium salt of F-1.6 diphosphate (F-1.6-DPBa$_2$).

EXAMPLE 2

5 g of Amberlite IRA-400 (OH form) was added to 50 ml of an aqueous solution containing 4.5 g (50 mmoles) of 1,3-dihydroxyacetone and 4.5 g (50 mmoles) of DL-lactaldehyde. The mixture was stirred at room temperature while the reaction was followed by chromatographic analysis (HPLC). After 10 minutes, the reaction was complete and the mixture was filtered to separate the resin, and the clear filtrate was concentrated under vacuum. 8.1 g (yield 90%) of an oily residue was thus obtained. HPLC analysis indicates a content in the mixture of 54% of 6-deoxy-D-fructose and 36% of 6-deoxy-L-sorbose.

We claim:

1. Process for the preparation of 6-deoxy-D-fructose and/or 6-deoxy-L-sorbose, characterized by the fact that
   a. Fructose-1,6-diphosphate or 1,3-dihydroxyacetone phosphate of the formula

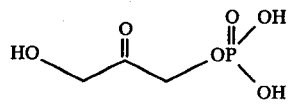

is treated with D- and/or L-lactaldehyde in the presence of an enzymatic system composed of aldolase and triose phosphate isomerase in an aqueous medium at pH 7.0, and
   b. The monophosphate salt thus obtained is hydrolyzed.

2. Process pursuant to claim 1, characterized by the fact that the aldolase and the triose phosphate isomerase used are coimmobilized on a solid support.

3. Process for the preparation of 6-deoxy-D-fructose and/or 6-deoxy-L-sorbose, characterized by the fact that 1,3-dihydroxyacetone is treated with D- and/or L-lactaldehyde in the presence of an anionic exchange resin.

* * * * *